United States Patent
Francis

(10) Patent No.: US 6,514,502 B1
(45) Date of Patent: Feb. 4, 2003

(54) PROPAGATION OF BOVINE CONONAVIRUS IN CHINESE HAMSTER OVARY CELLS

(75) Inventor: Michael J. Francis, Uxbridge (GB)

(73) Assignee: Schering-Plough Veterinary Corporation, Reno, NV (US)

( * ) Notice: Subject to any disclaimer, the term of this patent is extended or adjusted under 35 U.S.C. 154(b) by 0 days.

(21) Appl. No.: 09/491,202

(22) Filed: Jan. 25, 2000

Related U.S. Application Data

(60) Provisional application No. 60/117,317, filed on Jan. 26, 1999.

(51) Int. Cl.$^7$ .............................................. A61K 39/215
(52) U.S. Cl. ..................................... 424/221.1; 435/358
(58) Field of Search ............................ 435/5; 424/221.1

(56) References Cited

U.S. PATENT DOCUMENTS

| | | | |
|---|---|---|---|
| 5,514,376 A | 5/1996 | Giesa et al. | |
| 5,646,033 A | 7/1997 | Potash et al. | |
| 5,830,688 A | 11/1998 | Drillien et al. | |

FOREIGN PATENT DOCUMENTS

| | | | |
|---|---|---|---|
| WO | WO 95/34686 | 12/1995 | ............ C12Q/1/70 |

OTHER PUBLICATIONS

ATCC Catalog of Animal Viruses and Antisera, Chlamydiae and Rickettsiae, Sixth Ed., Buck, et al eds. (1990) p. 43.
ATCC Catalogue of Cell Lines and Hybridomas, Seventh Ed. Hay, et al eds. (1992) p. 36.
Baric, et al., 1997, J. of Virol. 71 (3):1946–1955.
Dinter & Morein, eds., Virus Infections of Vertebrates, 1990, vol. 3, Virus Infections of Ruminants, pp. 299–300.
Fields, et al., eds., 1990, Virology, 2$^{nd}$ Ed., Chap 29, Holmes, pp. 841–856.
Lathrop, et al; 1996, "Bovine Coronavirus Respiratory Infections in Feedlot Cattle", Conf. of Research Workers in Animal Diseases.
Smith, et al., Ohio State Univ. Bulletin, Animal Sciences Research and Reviews, Special Circular 156.
S. Dea et al., "Counterimmunoelectroosmophoresis for Detection of Neonatal Calf Diarrhea Coronavirus: Methodology and Comparison with Electron Microscopy," vol. 10, No. 2, pp. 240–244 (1979).
J.O. Fleming et al., "Pathogenic Characteristics of Neutralization–Resistant Variants of JHM Coronavirus (MHV–4)," *Adv. Exp. Med. Biol.*, vol. 218, pp. 333–342 (1987).
L.J. Saif et al., "Cell Culture Propagation of Bovine Coronavirus," *Journal of Tissue Culture Methods*, vol. 11, No. 3, pp. 129–145 (1988).
J. Storz et al., "Enhancement of Plaque Formation and Cell Fusion of an Enteropathogenic Coronavirus by Trypsin Treatment," *Infection and Immunity*, vol. 31, No. 3, pp. 1214–1222 (1981).
M.A. Sussman et al., "Immune Mediated Clearance of JHM Virus From the Central Nervous System," *Adv. Exp. Med. Biol.*, vol. 218, pp. 399–410 (1987).
T.E. Toth, "Trypsin–Enhanced Replication of Neonatal Calf Diarrhea Coronavirus in Bovine Embryonic Lung Cells," *Am. J. Vet. Res.*, vol. 43, No. 6, pp. 967–972 (1982).
Holmes, K. V., 1990, "Coronaviridae and their replication", in *Virology, Second Edition*, Fields, B. N., et al., eds., Raven Press, Ltd., New York, pp. 841–856.
American Type Culture Collection: Catalogue of animal viruses and antisera, chlamydiae and rickettsiae, Sixth Ed., 1990, Buck, C. and G. Paulino, eds., p. 43.

*Primary Examiner*—Laurie Scheiner
*Assistant Examiner*—Jeffrey S. Parkin
(74) *Attorney, Agent, or Firm*—Cynthia L. Foulke; Nancy V. Connelly

(57) ABSTRACT

The present invention provides methods for using Chinese hamster ovary (CHO) cells for the anchorage-dependent and suspension-culture propagation of coronaviruses, including bovine coronavirus. In one embodiment, bovine coronavirus VR874 is cultured in CHO-K1 cells under conditions in which the virus proliferates.

6 Claims, No Drawings

PROPAGATION OF BOVINE CONONAVIRUS IN CHINESE HAMSTER OVARY CELLS

CROSS-REFERENCE TO RELATED APPLICATION

This application claims priority under 35 U.S.C. § 119(e) from Provisional Application Ser. No. 60/117,317, filed Jan. 26, 1999 which is incorporated herein by reference in its entirety.

TECHNICAL FIELD

The present invention relates to methods for using Chinese hamster ovary (CHO) cells for the anchorage-dependent and suspension-culture propagation of coronaviruses, including bovine coronavirus.

BACKGROUND OF THE INVENTION

Bovine coronavirus (BCV) is a common cause of neonatal calf diarrhea, frequently afflicting calves aged two to four weeks. As a primary pathogen, BCV generally induces only a mild diarrhea. When combined with a secondary bacterial infection, however, BCV may become a major contributor to mortality in calves one month old and younger.

More recently, BCV has been implicated as a potential respiratory pathogen of older cattle, and it has been associated with outbreaks of winter dysentery in dairy cattle, as evidenced by the presence of BCV in the feces and BCV antibody seroconversion during such outbreaks.

There thus has been a need for culture systems to propagate BCV for the production of vaccines to prevent such cattle diseases.

Traditionally, BCV has been difficult to grow in cell culture, requiring an adaptation period following isolation. Many established cell lines are not suitable for growth of BCV, and much of the successfully reported propagation involves the use of primary cell cultures, which are unsuitable for large scale production. Furthermore, most coronaviruses show marked tissue tropism and will grow only in cells of the natural host species. See, e.g., Fleming et al., *Adv. Exp. Med. Biol.* 218:333–342 (1987); Sussman et al., *Adv. Exp. Med. Biol.* 218:399–410 (1987). Thus BCV is commonly grown in fetal bovine kidney cells, although it would be desirable to grow the virus instead in a more convenient established cell line.

In view of the economic importance of preventing BCV infections in cattle and the difficulties inherent in use of the cell culture systems commonly used to propagate the virus for vaccine production, there is a need for improved methods for growing BCV in culture.

SUMMARY OF THE INVENTION

The present invention fills the foregoing need by providing methods for the propagation of bovine coronavirus (BCV) in Chinese hamster ovary (CHO) cells. More particularly, this invention provides a method for propagating BCV comprising culturing CHO cells infected with BCV under conditions in which multiplication of the virus occurs.

In one embodiment, the CHO cells are CHO-K1 cells. In another, the BCV propagated is American Type Culture Collection strain ATCC VR-874. In another embodiment the CHO cells are grown in anchorage-dependent culture, while in another embodiment they are grown in suspension culture.

DESCRIPTION OF THE INVENTION

All references cited herein are hereby incorporated herein in their entirety by reference.

The present invention is based upon the surprising discovery that among various cell lines examined, CHO cells were uniquely suitable for efficiently growing BCV. Such cells were found to be particularly suitable for growing the virus in suspension culture, although they could also be used effectively attached to a suitable substrate.

Growth of BCV in CHO cells attached to a substrate can be carried out in all of the standard containers, including but not limited to tissue culture plates and flasks, roller bottles, and capillary assemblies or packed bed bioreactors in which BCV-infected cells attached to either capillary tubes or to other appropriate support matrices, e.g., glass beads or polymeric foams, are perfused with an appropriate culture medium, thereby permitting continuous harvesting of the virus from medium emerging from the capillary assembly or bioreactor. In the bioreactor systems, BCV-infected substrate-dependent CHO cells can be attached to polymeric microparticles. Alternatively, the CHO cells can be adapted by standard methods to grow independent of any substrate, maintained in suspension by agitation.

Culture medium that can be used in the present invention includes any of the media well known in the art to be useful for culturing CHO cells, including, e.g., Dulbecco's modified Eagle's medium (DMEM) and Glasgow's modified Eagle's medium (GMEM). Typically, such media are fortified by addition of an animal serum as a source of additional nutrients and growth factors. Examples of such animal sera suitable for use in this invention include, e.g., fetal calf serum (FCS) and adult bovine serum (ABS).

The present invention may also be practiced, however, using defined media, wherein the CHO cells are entirely weaned from the use of any animal serum. One example of such a defined medium that can be used is a basal medium such as DMEM containing hormonal and non-serum supplements, including albumin, insulin, transferrin and tryptose. Cells can be adapted to such a defined medium by continual passage in standard medium containing gradually reduced levels of serum, followed by transfer to mixtures of low serum and defined medium containing an increasing proportion of the defined medium.

The methods of this invention are applicable to the propagation of any BCV strain. Although a BCV called the Mebus strain and a field isolate from the United Kingdom were used to illustrate the invention in the Examples below, other isolates or other known strains could be used as well. Such known strains include, e.g., strains PQ, DB2, DBA, SD, 216XF, CN, BE, AW, OHC, SDC, JAZ, TS, BM, BW,L9, G110, F15, S1, S2, and CK.

Any CHO cell line can be used, including but not limited to the A2, A2H, XrS6, CHO-K1, CHO/dhFr, RR-CHOK1, UT-1, P22, CHO-1C6, Lec1, Lec2, Lec8, Pro-5, and DUKXB1 lines, although the CHO-K1 line deposited with the American Type Culture Collection under Accession No. ATCC CCL 61 is preferred. Similarly, a wide range of BCV can be propagated in the CHO cells, although propagation of the Mebus strain of BCV originally isolated from the feces of a calf afflicted with diarrhea in Nebraska, U.S.A. is described below for purposes of illustration of this invention.

To maximize the yield of virus produced, the CHO cells are preferably adapted to suspension culture using standard techniques, one example of which is illustrated below.

EXAMPLES

The present invention can be illustrated by the following examples. Unless otherwise indicated, percentages given below for solids in solid mixtures, liquids in liquids, and solids in liquids are on a wt/wt, vol/vol and wt/vol basis, respectively. Sterile conditions were generally maintained during cell culture.

Materials and General Methods

The Mebus strain of BCV (calf diarrheal coronavirus) was obtained from the American Type Culture Collection under Accession No. ATCC VR-874. For convenience, this virus is referred to below as BCV VR-874. A BCV field isolate obtained from the United Kingdom designated BCV MVB was also used.

Various cell lines examined for BCV propagation were grown in medium supplemented with adult bovine serum (ABS) instead of FCS. These cells included African green monkey kidney (Vero), Madin-Darby bovine kidney (MDBK), monkey fetal kidney (MA104), Madin-Darby canine kidney (MDCK), Syrian hamster kidney (BHK-21), mouse myeloma (NS0), and Human Rectal Adenocarcinoma (HRT-18) cells. Suspension culture cells included suspension-adapted CHO-K1 cells, and hamster kidney cells [designated BHK (Burg)].

Although MDCK cells are traditionally grown in ABS-supplemented medium, the CHO-K1, BHK-21, HRT-18, MDBK and Vero cells were initially grown in medium containing FCS but then adapted to growth in medium containing ABS, by gradually replacing the one serum with the other.

Dulbecco's Modified Eagle's Medium (DMEM) and Glasgow's Modified Eagle's Medium (GMEM) were obtained form Gibco, as were solutions of Polymixin B sulphate (10,000 $\mu$g/ml), Neomycin (10,000 $\mu$g/ml), trypsin-EDTA [(1×) 0.5 g Trypsin (1:250) and 0.2 g EDTA/liter in Modified Puck's Saline A], L-glutamine (200 mM), L15 Leibovitz medium, Dulbecco's Phosphate Buffered Saline (PBS 10×), Trypsin 2.5%, and Tryptose Phosphate Broth (TPB). FCS and ABS were obtained from Imperial Labs. L-Proline 1000× stock solution used at final concentration of 40 mg/liter was from Sigma Chemical Co., as were DEAE-Dextran (100× stock solution) and bovine albumin Fraction V. CHO cell medium for growing CHO-K1 cells in suspension culture was from PAA Biologics. Agarose Sea Plaque was obtained from Flowgen Instruments Ltd. Rat blood in Alsever's solution was from Serotec.

Media formulations used for the growth of various cell lines are indicated in the following Table:

TABLE 1

| Ingredient | Medium 1 | Medium 2 | Medium 3 |
| --- | --- | --- | --- |
| DMEM | 100 ml | 100 ml | |
| GMEM (BHK-21 medium) | | | 100 ml |
| L-glutamine | 1.0 ml | 1.0 ml | |
| Tryptose Phosphate Broth | | | 10.0 ml |
| Polymixin B sulphate | 0.5 ml | 0.5 ml | 0.5 ml |
| Neomycin | 0.5 ml | 0.5 ml | 0.5 ml |
| Fetal Calf Serum | 10.0 ml | | 10.0 ml |
| Adult Bovine Serum | | 10.0 ml | |
| Cell line grown | MDBK, NS0, MA104, Vero [CHO K1 (monolayer) with addition of 40 $\mu$g/ml L-Proline] | MDCK | BHK-21, BHK (BURG) |

All cell lines were revived from storage in liquid nitrogen and passaged several times in the appropriate medium. Anchorage-dependent CHO-K1, MA104, MDBK, NS0, MDBK and Vero cells were adapted to grow in DMEM, while BHK-21 cells were grown in GMEM. Cell growth was monitored using viable cell counts and microscopic observation. Cells were grown to confluence and split at an appropriate ratio at each passage. Once healthy cell growth was established, virus titrations were performed on the anchorage dependent cells.

CHO-K1 suspension cells were grown in CHO medium without any further additions. Suspension cells were grown in spinner flasks and directly inoculated with BCV.

Virus titrations in cultures of the various anchorage-dependent cell lines were carried out using 24-well plates with confluent monolayers of the cells, essentially as follows. BCV was diluted 1/10 in DMEM with and without trypsin added to a final concentration of 10 $\mu$g/ml. The effect of trypsin was investigated due to reports suggesting that its presence both enhanced virus replication and facilitated growth in some cell lines otherwise considered non-permissive. See, e.g., Dea et al., *J. Clin. Microbiol.* 10:240–244 (1980); Storz et al., *Infect. Immun.* 31:1214–1222 (1981); Toth, *Am. J. Veterinary Res.* 43:967–972 (1982).

After incubation at 37° C. for 1 hour, the virus was diluted to $10^{-2}$, $10^{-3}$, and $10^{-4}$. Growth medium was removed from the plates and 100 $\mu$l each virus dilution were added to the wells. The plates were incubated for 1 hour at 37° C. with gentle rocking to ensure that the virus was evenly spread across the plate.

Following the incubation, the inoculum was removed and 1 ml of overlay medium (L15 medium containing 2% FCS and 1% agarose) was added to each well. Plates containing the trypsin-treated virus had L15 medium containing 2% FCS, 1% agarose plus trypsin and 50 $\mu$g/ml DEAE-Dextran added to each well. The plates were incubated for 8 days at 37° C. in 5% $CO_2$ and then examined microscopically for the presence or absence of cytopathic effects (CPE).

The plates were incubated for 8 days at 37° C. in 5% $CO_2$ and then examined microscopically for the presence or absence of cytopathic effects (CPE). Observed CPE typically included cellular granulation, syncytial formation and cell lysis.

A duplicate set of plates had 1 ml of L15/2% FCS medium without agarose added to the wells. After incubation at 37° C. for 8 days as above, the medium was removed and assayed for haemagglutination activity. This was accomplished by titrating 50 $\mu$l double dilutions of virus across a V-bottomed microtitre plate. 1 ml of rat blood cells (Serotec) was washed twice in 0.5% Bovine Serum Albumin/Phosphate Buffered Saline (0.5% BSA/PBS) and then centrifuged to sediment the cells. The resulting packed cell volume was diluted in 15 ml of 0.5% BSA/PBS to produce a 0.25% suspension. Fifty microliters of a 0.25% rat red cell suspension were added to each well, and the degree of haemagglutination was scored after 1 hour at room temperature.

Wells containing a mat of red cells formed on the base were scored as positive for haemagglutination, and wells in which the red cells ran to the bottom of the well to form a small button were scored as negative. The haemagglutination titer was defined as the highest dilution where complete agglutination of the red cells was observed.

Virus titrations in suspension cultures of BHK (Burg) and CHO-K1 cells were performed by splitting the cells into 30 ml conical-bottomed Universal containers and sedimenting the cells by low speed centrifugation. The supernatant fluids were discarded and the remaining pellets were resuspended in 1 ml of GMEM per Universal container.

BCV was prepared by growth in CHO-K1 anchorage-dependent cells for 8 days. The harvest was clarified by centrifugation at 3000 rpm for 5 minutes. The BCV was then diluted 1/20, 1/200 and 1/10,000 in GMEM medium, and the BHK-21 (Burg) cells were infected at 1/20 and 1/200; the CHO-K1 cells were infected at 1/200 and 1/10,000. The cells were incubated with the virus at 37° C. for 1 hour. Control cells were inoculated with virus growth medium to simulate infection.

Duplicate Universals of the BHK-21 (Burg) cells were resuspended in 25 ml of GMEM containing 10% TPB and Neomycin/Polymixin with or without 2% FCS. The CHO-K1 cells were resuspended in 25 ml of CHO medium. Contents from each Universal were transferred to 125 ml conical flasks and placed in a shaker incubator at 35° C. The cultures were sampled daily and tested for haemagglutination activity.

BCV Proliferation is Supported by CHO-K1 Cells

The proliferation of United Kingdom field isolate BCV MVB was examined on confluent monolayers of anchorage-dependent CHO-K1, MA104, MDCK, BHK-21, Vero and MDBK cells. Virus titers were determined by haemagglutination and CPE assays essentially as described above, with the following results.

TABLE 2

Results 8 Days Post-infection

| Cell line | Virus used | Haemagglutination titers in T25 flasks | *CPE in 24-well virus titration plates |
|---|---|---|---|
| CHO-K1 | BCV MVB | 1024–2048 | CPE detected at virus dilutions $10^{-1}$ and $10^{-2}$ None detected at virus dilutions $10^{-3}$ and $10^{-4}$ |
| MA104 | BCV MVB | <2 | None detected at virus dilutions $10^{-1}$, $10^{-2}$, $10^{-3}$, $10^{-4}$ |
| MDCK | BCV MVB | <2 | None detected at virus dilutions $10^{-1}$, $10^{-2}$, $10^{-3}$, $10^{-4}$ |
| BHK-21 | BCV MVB | <2 | None detected at virus dilutions $10^{-1}$, $10^{-2}$, $10^{-3}$, $10^{-4}$ |
| MDBK | BCV MVB | <2 | None detected at virus dilutions $10^{-1}$, $10^{-2}$, $10^{-3}$, $10^{-4}$ |
| Vero | BCV MVB | <2 | None detected at virus dilutions $10^{-1}$, $10^{-2}$, $10^{-3}$, $10^{-4}$ |
| All Cell Line Controls | No virus | <2 | None detected |

*There was no difference in CPE with/without trypsin addition to medium and virus.

The results in Table 2 show that the BCV grew well only in the CHO-K1 cells; viral proliferation was undetectable in the other cells. Similar results were obtained using BCV VR-874, as can be seen from Table 3. The virus in this case was not treated with trypsin prior to infection. Virus growth was compared between titration plates containing DMEM based overlay medium and plates containing L15 overlay medium, and virus growth was expressed as haemagglutination activity.

TABLE 3

Results 6 Days Post-infection

| | | Haemagglutination Titer | |
|---|---|---|---|
| Cell Line | Virus Dilutions | DMEM | L15 |
| CHO-K1 | $10^{-1}$ | 2048 | 1024 |
| | $10^{-2}$ | 2048 | 1024 |
| | $10^{-3}$ | 2048 | 1024 |
| | $10^{-4}$ | 2048 | 1024 |
| | $10^{-5}$ | 2048 | <2 |
| | $10^{-6}$, $10^{-7}$, $10^{-8}$ | <2 | <2 |
| MDCK | $10^{-1}$, $10^{-2}$, $10^{-3}$, $10^{-4}$, $10^{-5}$, $10^{-6}$, $10^{-7}$, $10^{-8}$ | <2 | <2 |
| BHK-21 | $10^{-1}$ | 8 | 16–32 |
| | $10^{-2}$, $10^{-3}$, $10^{-4}$, $10^{-5}$, $10^{-6}$, $10^{-7}$, $10^{-8}$ | <2 | <2 |
| MDBK | $10^{-1}$, $10^{-2}$, $10^{-3}$, $10^{-4}$, $10^{-5}$, $10^{-6}$, $10^{-7}$, $10^{-8}$ | <2 | <2 |
| Vero | $10^{-1}$, $10^{-2}$, $10^{-3}$, $10^{-4}$, $10^{-5}$, $10^{-6}$, $10^{-7}$, $10^{-8}$ | <2 | <2 |
| All Cell Line Controls | No Virus | <2 | <2 |

One other isolate designated BCV WVB that was derived from BCV MVB was found to grow in both Vero and CHO-K1 cells. The characteristics of that virus, however, made it unsuitable for use in a vaccine.

Although the data in the foregoing Tables were produced using culture medium supplemented with fetal calf serum, proliferation of BCV VR-874 in CHO-K1 cells was also demonstrated using adult bovine serum as well, and even using a chemically-defined medium with no serum supplement. For example, proliferation of BCV MVB was obtained in suspension-adapted CHO-K1 cells grown in DMEM based serum-free medium.

BCV Proliferation in Suspension Culture

The proliferation of BCV MVB in suspension-adapted CHO-K1 cells grown in DMEM based serum free medium was demonstrated by determining virus titers by haemagglutination as described above and by infectivity using a plaque assay. Virus samples were titrated in a ten-fold dilution series in DMEM containing 10% tryptose phosphate broth and 40 µg/ml L-proline. Twenty-five microliters of each dilution were added to separate wells of a 24-well cell culture plate seeded with $10^5$ anchorage-dependent CHO-K1 cells 24 hours previously. After incubation at 37° C. for 1 hour, the wells were overlayed with DMEM containing 2% FCS, 10 % tryptose phosphate broth, 40 µg/ml L-proline and 1% sea plaque agarose. The plates were incubated at 37° C. for 7 days and then fixed with 10 % formalin in PBS for 1 hour, and the plaques were visualized by haemadsorption following the addition of 0.5 ml of 1% rat red cells per well. The results following harvest 7 days post infection were as shown in Table 4.

TABLE 4

| Multiplicity of Infection | 0.2 | 0.02 | 0.002 | 0.0002 | Negative Control |
|---|---|---|---|---|---|
| HA Titer | 4,096 | 4,096 | 4,096 | 4,096 | <40 |
| Infectivity Titer | $1.1 \times 10^7$ | $1.1 \times 10^7$ | $9.5 \times 10^6$ | $4.0 \times 10^6$ | <40 |

Similar results were obtained following infection of suspension-culture-adapted CHO-K1 cells with BCV VR-874, as can be seen in the following Table.

TABLE 5

Haemagglutination Titers at Various Times Following Infection

| Cell Line | Virus Dilution (2) | \multicolumn{4}{c}{Number of Days Post-infection} | | | |
|---|---|---|---|---|---|
| | | 2 | 3 | 4 | 7 |
| BHK (Burg) | 1/20 | 8 | 64 | 16 | 8 |
| | 1/200 | <2 | 32 | 2 | 2 |
| (1) BHK (Burg) with 2% FCS | 1/20 | 8 | 32 | 16 | 8 |
| | 1/200 | 2 | 32 | 4 | 4 |
| CHO-K1 | 1/200 | 32 | 2048 | 4096 | 4096 |
| | 1/10,000 | 2–4 | 128 | 32 | 16 |

All cell controls <2
(1) Fetal Calf Serum was added to the virus maintenance medium
(2) Dilution of virus used at infection As is evident from Table 5, CHO-K1 cells supported the growth of BCV VR-874 far better than did BHK (Burg) cells.

Thus whether in anchorage-dependent or suspension culture, CHO cells are an effective host cell for the propagation of BCV.

Many modifications and variations of this invention can be made without departing from its spirit and scope, as will be apparent to those skilled in the art. The specific embodiments described herein are offered by way of example only, and the invention is to be limited only by the terms of the appended claims.

What is claimed is:

1. A method for propagating a bovine coronavirus in Chinese hamster ovary cells comprising:

(a) culturing said Chinese hamster ovary cells with cell culture medium;

(b) inoculating said Chinese hamster ovary cells with the bovine coronavirus;

(c) incubating the inoculated Chinese hamster ovary cells; and, (d) harvesting said bovine coronavirus from said medium.

2. The method of claim 1 in which the Chinese hamster ovary cells are in anchorage-dependent or suspension culture.

3. The method of claim 1 in which the Chinese hamster ovary cells are CHO-K1 cells.

4. The method of claim 1 in which the bovine coronavirus is VR-874.

5. The method of claim 1 in which the cells are cultured in serum-free medium.

6. A method for propagating a bovine coronavirus strain designated ATCC VR-874 in CHO-K1 cells comprising:

(a) culturing said CHO-K1 cells with cell culture medium;

(b) inoculating said CHO-K1 cells with the bovine coronavirus strain ATCC VR-874;

(c) incubating the inoculated CHO-K1 cells; and, (d) harvesting said bovine coronavirus strain ATCC VR-874 from said medium.

* * * * *

UNITED STATES PATENT AND TRADEMARK OFFICE
CERTIFICATE OF CORRECTION

PATENT NO. : 6,514,502 B1  Page 1 of 1
DATED : February 4, 2003
INVENTOR(S) : Michael J. Francis It is certified that error appears in the above-identified patent and that said Letters Patent is hereby corrected as shown below:

<u>Title page, Item [54] and Column 1, line 1,</u>
"CONONAVIRUS" to read -- CORONAVIRUS --.

Signed and Sealed this

Sixteenth Day of September, 2003

JAMES E. ROGAN
*Director of the United States Patent and Trademark Office*